United States Patent [19]

Lubecki et al.

[11] 4,224,517
[45] Sep. 23, 1980

[54] DEVICE FOR ASSAYING URANIUM AND/OR THORIUM IN ORE SPECIMENS COMPRISING GOLD FOIL FOR SUPPRESSING COMPTON BACKGROUND

[75] Inventors: Andrzej Lubecki, Stutensee; Klaus Rieber, Eggenstein-Leop, both of Fed. Rep. of Germany

[73] Assignee: Kernforschungszentrum Karlsruhe GmbH, Karlsruhe, Fed. Rep. of Germany

[21] Appl. No.: 915,778

[22] Filed: Jun. 15, 1978

[30] Foreign Application Priority Data

Jun. 22, 1977 [DE] Fed. Rep. of Germany ....... 2727989

[51] Int. Cl.² ..................... G01N 23/20; G01N 33/20; G01N 23/223; H01J 37/20
[52] U.S. Cl. .................................... 250/272; 250/450; 250/456; 250/510
[58] Field of Search ............... 250/272, 490, 450, 451, 250/456, 452, 510

[56] References Cited

U.S. PATENT DOCUMENTS

| | | | |
|---|---|---|---|
| 3,404,275 | 10/1968 | Martinelli | 250/272 |
| 3,889,113 | 6/1975 | Rhodes | 250/272 |
| 4,063,089 | 12/1977 | Gaurba | 250/272 |

*Primary Examiner*—Alfred E. Smith
*Assistant Examiner*—T. N. Grigsby
*Attorney, Agent, or Firm*—Spencer & Kaye

[57] ABSTRACT

A device for assaying uranium and/or thorium present in ore specimens in concentrations above approximately 20 ppm according to the energy dispersive X-ray fluorescence technique, including a support for holding an ore specimen and a gamma source detector system located below the support and including a source for directing gamma radiation into the specimen in order to excite radiation containing X-ray K-lines, and a detector for detecting the X-ray K-lines of such radiation.

3 Claims, 3 Drawing Figures

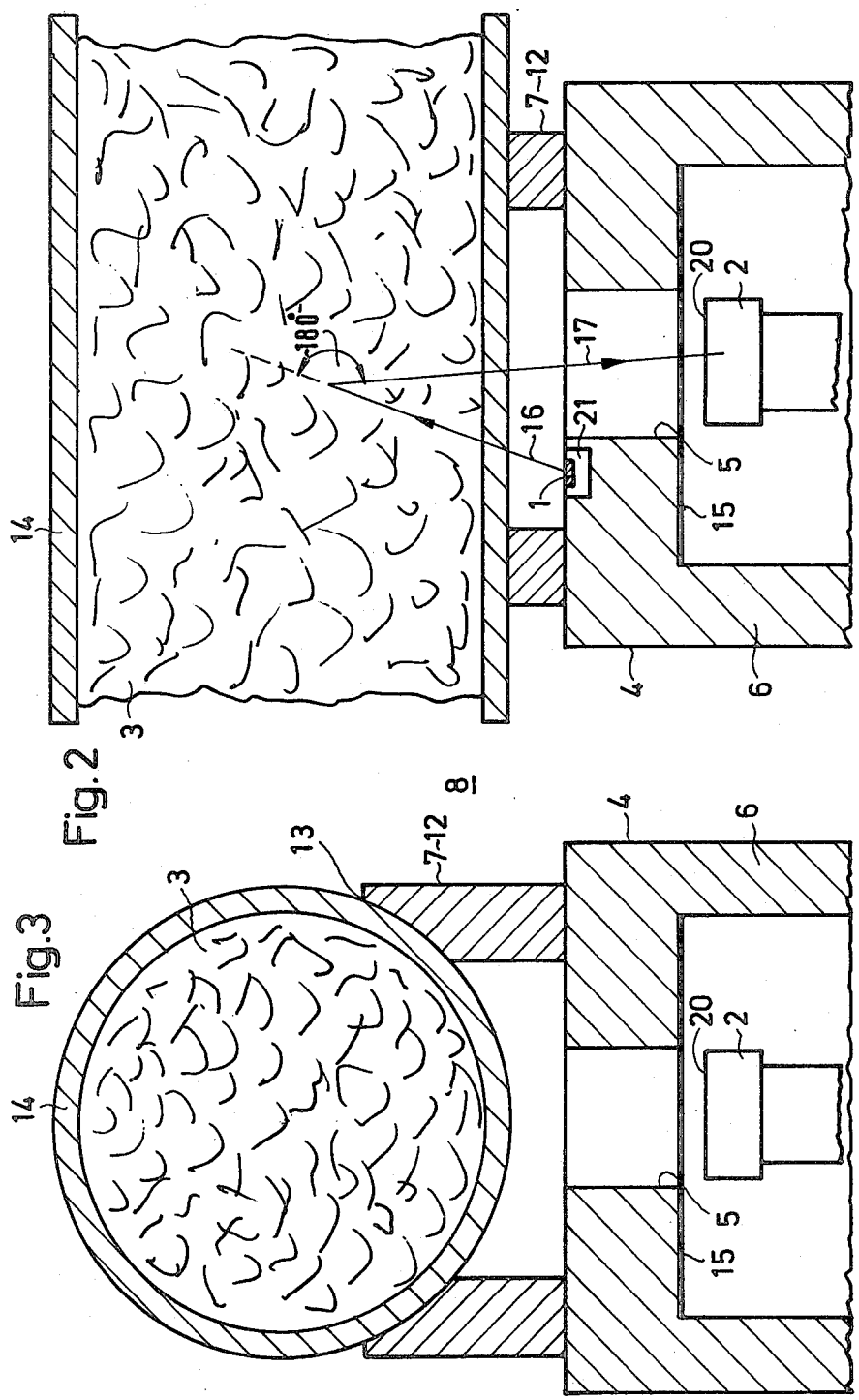

DEVICE FOR ASSAYING URANIUM AND/OR THORIUM IN ORE SPECIMENS COMPRISING GOLD FOIL FOR SUPPRESSING COMPTON BACKGROUND

BACKGROUND OF THE INVENTION

The invention relates to a device for assaying uranium and/or thorium in ore specimens in concentrations exceeding approx. 20 ppm by means of the energy dispersive X-ray fluorescence technique.

A detailed description of the analytical techniques presently employed in uranium ore analysis with extensive literature references is found in the book "Kernchemie in Einzeldarstellungen," vol. 5, by Herbert Sorantin, Verlag Chemie 1975. The techniques employed range from X-ray spectrometry, gamma- and alpha-spectrometry through chromatography, gravimetry and polarography up to spectro-photometry and fluorimetry.

The techniques described and used, respectively, have the following drawbacks from the point of view of ore analysis:
 extensive preparation and small quantities of the specimens
 long span of time between sampling and analtyical result
 depending on the technique used, dependency of the analytical error on the matrix composition, the ore age, or the subjective decision of the person carrying out the analysis.

SUMMARY OF THE INVENTION

An object the invention is to provide a fast analytical technique capable of automation with the necessary equipment allowing assays for uranium and/or thorium in powderized ore specimens or as drilling cores over as broad a range of concentration as possible with a limit of detection beginning at 20 ppm.

Under the invention this problem is solved by arranging the ore specimens in a support above a gamma source detector system in such a way that the X-ray K-lines initiated in the ore specimens by irradiation from the gamma source become measurable.

In an advanced embodiment of the device according to the invention, a collimator with an aperture is arranged between the gamma source and the detector of the system, the gamma source is attached to or in the collimator wall close to the aperture and the support for the ore specimens is arranged around the aperture in such a way that the gamma source is also enclosed and shielded relative to the environment.

In some particularly advantageous embodiments of the invention this support consists of a cylinder to the free front of which a specimen container can be attached or the support consists of a cylinder with a saddle-shaped recess to accommodate a drilling core section. To suppress the Compton background the aperture may be closed with a gold foil.

In the invention the well-known principle of X-ray fluorescence is applied, but instead of using the X-ray L-lines, as usual, the k-series of uranium and/or thorium is excited. This is possible only if the X-ray lines are excited by gamma radiation emitted by radionuclides, because the familiar X-ray tubes cannot be used for this range of energy. $^{57}$Co is a radionuclide which, e.g., constitutes a suitable source of excitation. The excited X-ray spectrum is recorded by a very high purity germanium solid state detector which, in addition, meets the following criteria: maximum resolution in the energy range of the uranium and thorium K-series, respectively, in the energy range of 90 keV to 120 keV and, if possible, good peak/Compton ratio associated with a high response probability in the energy range mentioned above.

The major advantages of the invention arise from the fact that the use of the X-ray K-series of uranium and/or thorium excited by gamma radiation from the radionuclide source and a measuring setup tailored to the problem at hand and optimized experimentally (source-detector-specimen geometry, choice of detector, of collimators and shielding) and filtration of the excited spectrum by the gold filter with a thickness optimized experimentally among other results also makes the analytical result independent of the density of the specimen in the density range between 1.3 g/cm$^3$ and 3.5 g/cm$^3$.

The invention allows fast, automatic assays for uranium and/or thorium in pulverized ore specimens or in drilling cores in a concentration range of approx. 20 ppm to more than 5% of uranium or thorium. The analysis (in contrast to analyses using X-ray L-lines) is independent of the specimen matrix and can be carried out in a field laboratory even by unqualified personnel. The large mass of the specimens analyzed simplifies representative sampling and renders the analytical result independent of any microinhomogeneities in the material analyzed.

Because of the short time required for analysis it is possible to carry out several uranium and thorium assays, respectively, per hour. This means a much larger number of specimens analyzed per annum compared with the methods presently used and also implies lower costs per analysis.

In the exploration phase the quick availability of analytical results means an immediate and specific feedback on the sampling site. The acceleration of the whole exploration compaign which this brings about improves the economics of a project.

BRIEF DESCRIPTION OF THE DRAWINGS

FIGS. 1 and 2 are elevational, cross-sectional views of two embodiments of the invention.

FIG. 3 is an elevational, cross-sectional view of the embodiment of FIG. 2, in a plane normal to that of FIG. 2.

DESCRIPTION OF THE PREFERRED EMBODIMENTS

Figure 1:
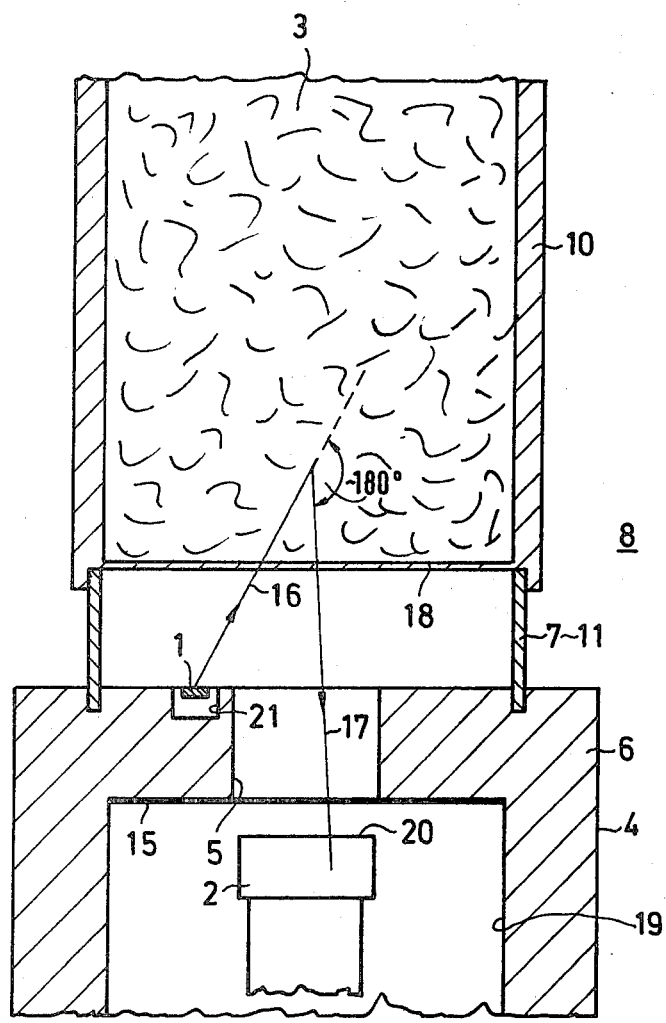

FIG. 1 shows the general arrangement of a device according to the invention for measuring a powder specimen. The specimen was ground to a particle size of less than 100 μm and filled into a specimen holder 10. The specimen holder 10 is attached to a support 7 designed as a spacer ring 11 and at the same time serving to shield the environment 8 against gamma radiation 16 emitted by the source 1. Moreover, the spacer ring 11 is arranged concentrically around the aperture 5 of a collimator arrangement 6 consisting of absorber material. The recess 19 of the collimator 6 contains the detector 2, the inlet area 20 of which faces the aperture 5. The aperture 5 is also closed by a gold foil 15. It serves to suppress the Compton background of the radiation 17 reaching the detector 2 from the specimen 3 through the aperture 5. This X-radiation 17 with the X-ray K-lines is excited by the gamma radiation 16 in specimen 3.

The gamma source 1 consists of an enclosed $^{57}$Co pellet arranged in a recess 21 in the collimator wall 6 close to the aperture 5. The geometry of the recess 21 with the gamma source 1 relative to the aperture 5 is determined by optimization requirements. The gamma radiation 16 and the X-radiation 17 should be arranged at an angle of 180° relative to each other.

Criteria to be met by detector 2 are an optimum measuring geometry and specimen size and thickness of the gold foil 15. The optimization criterion is the ratio between the signal (net peak area of the uranium K alpha 1 line) relative to the background in the spectrum recorded. The distance between the aperture 5 and the bottom 18 of the container 10 is 20 mm, the collimator aperture has a diameter of 23 mm and is 18 mm deep. The gold foil 15 has a thickness of 100μ. The inlet area 20 measures 200 mm$^2$; the thickness of the detector 2 is 5 mm.

FIGS. 2 and 3 show two sections through the same measuring setup arranged normal to each other, but the support 7 in this case is designed to the use of a drilling core 14 as specimen 3. For this purpose, the support 7 is designed as a cylinder 12 with a saddle-shaped recess 13 (see FIG. 3) into which the tube 14, which is also cylindrical, with its filling is put horizontally. The distance between the wall of the drilling core 14 and the aperture 5 in the collimators 4 and 6, respectively, is consequently reduced to 10 mm.

The wall thickness of the shielding cylinder 12 made of stainless steel is dimensioned so that it again acts as a shield relative to the environment 8. Relative to the spacer ring 11 in the first embodiment shown in FIG. 1, it is overdimensioned in this case for reasons of strength. The source strength of the gamma source 1 is 1 to 10 mCi, the gamma radiation 16 emitted by it has an energy of appox. 122 keV, while the K-alpha-1-radiation in the X-radiation 17 has an energy of approx. 98 keV.

For control and monitoring of the measurements and for executing spectra evaluations and concentration calculations there is a mini process computer (not shown in more detail). The specimen necessary for calibration is synthetically manufactured out of $UO_2$ and $SiO_2$. For the analysis a container (not shown in more detail) with the accurate amount of calibration specimen filled in is put on the specimen support 7. When working with different specimen masses also the weight must be input to the mini process computer, otherwise it is sufficient to fix this mass once in the calibration step.

We claim:

1. A device for assaying uranium and/or thorium present in ore specimens in concentrations above approximately 20 ppm according to the energy dispersive X-ray fluorescence technique, comprising: a support member for supporting an ore specimen; and a gamma source detector system located below said support member and including a gamma source supplying gamma radiation to the specimen in order to produce, in the specimen, radiation containing X-ray K-lines, a detector disposed for detecting the X-ray K-lines of the radiation from the specimen, a collimator provided with an aperture located between said gamma source and said detector, said gamma source being secured at a wall of said collimator close to said aperture, and a gold foil member extending across, and closing, said aperture, in order to suppress the Compton background, and wherein said support member surrounds said aperture and encloses said source in order to shield said source relative to the surrounding environment.

2. A device as defined in claim 1 wherein said support member is in the form of a cylinder presenting a free front end arranged for holding a specimen container.

3. A device as defined in claim 1 wherein said support member is in the form of a cylinder presenting a saddle-shaped recess for receiving a section of a drilling core.

* * * * *